United States Patent

Lazaro Muñoz et al.

Patent Number: 5,264,648
Date of Patent: Nov. 23, 1993

[54] PROCESS FOR THE OBTAINMENT OF A LIGHT PARAFFIN ISOMERIZATION CATALYST

[75] Inventors: Jesûs J. Lazaro Muñoz, Madrid; Avelino Corma Canos, Valencia; Juana M. Frontela Delgado, Madrid, all of Spain

[73] Assignee: Compania Espanola De Petroleos, S.A.—CEPSA, Madrid, Spain

[21] Appl. No.: 742,602

[22] Filed: Aug. 8, 1991

Related U.S. Application Data

[62] Division of Ser. No. 548,227, Jun. 29, 1990, Pat. No. 5,057,471.

[30] Foreign Application Priority Data

Jul. 19, 1989 [ES] Spain ................... 89025553

[51] Int. Cl.⁵ .............................. C07C 5/13
[52] U.S. Cl. .................. 585/739; 585/750; 585/751
[58] Field of Search ............ 585/739, 750, 751; 502/66, 74, 78

[56] References Cited

U.S. PATENT DOCUMENTS

| | | | |
|---|---|---|---|
| 4,835,129 | 5/1989 | Travers et al. | 585/739 |
| 4,935,578 | 6/1990 | Dufresne et al. | 585/739 |
| 4,954,243 | 9/1990 | Kuehl et al. | 585/653 |
| 5,057,471 | 10/1991 | Munoz et al. | 502/66 |
| 5,073,668 | 12/1991 | Hertzenberg et al. | 585/739 |

*Primary Examiner*—Anthony McFarlane
*Assistant Examiner*—Nhat Phan
*Attorney, Agent, or Firm*—Darby & Darby

[57] ABSTRACT

The invention refers to a process for the obtainment of a catalyst useful in the isomerization of light paraffins, fundamentally based on acid treatment of a synthetic mordenite at temperatures between 40° and 100° C. followed by treatment with steam-air at temperatures between 300° and 600° C. which make it possible to optimize the $SiO_2/Al_2O_3$ framework ratio and the amount of extraframework aluminum of the zeolite. The mordenite thus obtained is mixed with an inorganic refractory oxide such as $Al_2O_3$ and a metal of group VIII, basically Pt, is added in an amount between 0.1 and 0.5% by weight referred to the final catalyst.

The catalyst has been tested in the isomerization of light refinery fractions ($C_5$ and $C_6$) and has a high activity and selectivity of branched isomers with a low production of gases and a high octane number for the light gasoline obtained.

3 Claims, 1 Drawing Sheet

PROCESS FOR THE OBTAINMENT OF A LIGHT PARAFFIN ISOMERIZATION CATALYST

This is a division of application Ser. No. 548,227, filed Jun. 29, 1990, now U.S. Pat. No. 5,057,471.

The present invention refers to a process for the obtainment of a new catalyst for isomerization of light paraffins based on a modified synthetic mordenite in which the $SiO_2/Al_2O_3$ framework ratio and the amount of extraframework Al have been optimized by specific acid and steam treatments. The zeolite mixed with a refractory material oxide and, at least, with one metal of group VIII is calcined giving rise to the final catalyst.

PRIOR ART

The isomerization reaction of light paraffins is of considerable importance in the petroleum industry due to the present demand for unleaded gasoline which imposes modification of legislation concerning the environment in industrialized countries. Since light straight run is an important ingredient of the blending of gasolines, the increase of the octane number of this fraction by means of catalytic isomerization processes is of vital importance.

Of the catalysts used the most up to now for the isomerization of light, straight run, Friedel-Crafts type, nobel metal on fluorinated or chlorinated aluminas and nobel metal on zeolitic supports, these last ones have created the most interest in the last few years. The advantages that the zeolitic catalysts have over the above cited ones are simplicity of operation, the absence of additional problems of corrosion and a greater resistance to sulfur.

Most of the catalysts described up until now consist of modified zeolites, fundamentally mordenite, mixed with an inorganic refractory oxide such as $Al_2O_3$ and with a noble metal impregnated or exchanged on the zeolite, on the alumina or on a mixture of both of them.

Mordenite is a zeolite with a structure in monodimensional channels. The diameter and type of channels, as well as the structure, is well established in the prior art.

Numerous processes have been described to convert natural or synthetic mordenite into the active acid form in isomerization. Treatment with ammonium ions with subsequent calcination (U.S. Pat. No. 3,190,939) and acid treatment prior to exchange with $NH_4^+$ and calcination (U.S. Pat. No. 3,442,794 SHELL) make it possible to pass from the $Na^+$ form of the mordenite to the protonic form.

On the other hand, numerous processes to increase the acidity of the mordenite, based on the partial dealuminization of the crystalline structure, have also been described.

By means of acid treatments it is possible to increase the $SiO_2/Al_2O_3$ ratio of the mordenite and its activity in isomerization. Thus, U.S. Pat. Nos. 3,507,931 (MORRIS) and 4,018,711 (BERTOLACINI) describe an improvement in the capacity of isomerization of mordenite with a silica-alumina ratio of at least 20:1 and 19:1 respectively, obtained by acid treatments. The acid attack of zeolite with solutions that contain $Na^+$ and $K^+$ ions (U.S. Pat. No. 4,400,576 SHELL) and with very severe acid treatments: for ex. 12N HCl, 100° C. (U.S. Pat. No. 3,480,539 ESSO) to produce its dealuminization, has also been described.

By thermal treatments with steaming and by selfsteaming followed by acid attack (U.S. Pat. No. 3,506,400 ESSO), (U.S. Pat. No. 3,551,353 MOBIL) higher levels of dealuminization in the mordenite are obtained, thus $SiO_2/Al_2O_3 \geqq 35$ and up to 100 in the patent filed by MOBIL.

Other dealuminization processes with $Cl_4Si$ which replaces aluminiums by silicons in the framework of the mordenite causing stability not to be lost have also been described in the prior art (U.S. Pat. No. 4,273,753 MOBIL.)

Finally, other methods to increase the acidity of the mordenite such as treatment with halogenated compounds have been previously patented (U.S. Pat. No. 3,413,370 UPO), (U.S. Pat. No. 3,932,554 NIPPON OIL.)

Acid treatments of mordenite alone cannot attain a very thorough dealuminization without the risk of breaking the structure and washing alone in the washing the extraframework aluminum produced. The same thing happens for acid treatment with $Na^+$ and $K^+$ competing ions. Thermal treatments with steaming give rise to higher $SiO_2/Al_2O_3$ framework ratios but the extraframework aluminum produced can clog up the channels and prevent free access of the reagents to the acid centers.

Washing with acid the zeolite subjected to steaming can "clean" the channels washing away the extraframework Al produced in the previous process.

Several authors have described maximums of activity for isomerization in terms of the $SiO_2/Al_2O_3$ framework ratio. Voorhies and Bryan (Aiche. J. 852 (1968)) have found a maximum of activity for isomerization of $C_5$ at a $SiO_2/Al_2O_3$ ratio of 17:1; said value has been subsequently confirmed by the studies of Koradia et al. (J. Cat, 66, 290 1980.) Bremer et al. (Procd. of the symp. of zeolites, Szeged, Hungary, September 1978) put the maximum of activity at a ratio of 23:1 for hydrocracking of n and isooctane. These studies concluded that an increase of the number of strong Bronsted centers increased the activity of the catalyst.

Regarding the deposition of noble metal to carry out the hydrogenating function of the catalyst, the preferred metal is Pt in almost all patents and the preferred method is the impregnation method, either on mordenite or on alumina and subsequent mixing with the zeolitic material (U.S. Pat. No. 4,400,576 SHELL.)

Processes for a better dispersion of Pt introducing competitors in the impregnation process and treating the final catalyst in a stream of air with chlorinated compounds have also been described (E.P. 0256945 IFP.)

The deposition of another metal (Zr) along with Pt has also been described to improved the isomerizing activity of the catalyst (E.P. 0253743 TOTAL.)

OBJECT OF THE INVENTION

The synergic effect that the extraframework Al can have on the Bronsted acid centers of zeolite has been described in literature (C. Mirodatos, D. Barthomeft "J. Chem. Comun 39, 1981"; A. Corma, V. Fornes, O. Pallota and F. Melo "Innovation in Zeolites, New Port 1987"; R. M. Lago, W. O. Haag, R. J. Mikousky, D. H. Olson, F. D. Hellring, K. D. Schmitt, G. T. Kerr "7th. Int. Zeolite Conference 1986,") and it can be attributed to the electronegativity of the polymerized $AlO^+$ species that contribute to a greater polarization of the O-H bond.

In the present invention a mordenite with an optimum Al framework:Al extraframework ratio is attained to the extent that no obstruction is produced in the channels and the effect of improvement of the activity of the above mentioned extraframework species is taken advantage of.

For this purpose a mordenite with a low Na+ content is treated with an acid solution to obtain a $SiO_2/Al_2O_3$ ratio between 15 and 22 (framework) and subsequently it is heated in a controlled steam-air atmosphere to obtain a dealuminized mordenite with a $SiO_2/Al_2O_3$ ratio = 15–40 (network) and with a controlled amount of extraframework Al.

Due to the effect of this extraframework Al a maximum of activity for isomerization of light straight run is attained at a higher $SiO_2/Al_2O_3$ framework ratio than in the above cited studies in which very low activities were obtained for this ratio (30:1.) Besides higher $SiO_2/Al_2O_3$ ratios produce a smaller amount of coke thus lengthening the life of the catalyst.

These catalysts can be used in the isomerization of $C_4$ to $C_7$ light paraffins and particularly in the refinery LSR fraction and have a high level of conversion to isoparaffins with a low production of gases coming from cracking reactions.

DESCRIPTION OF THE INVENTION

Figure 1:
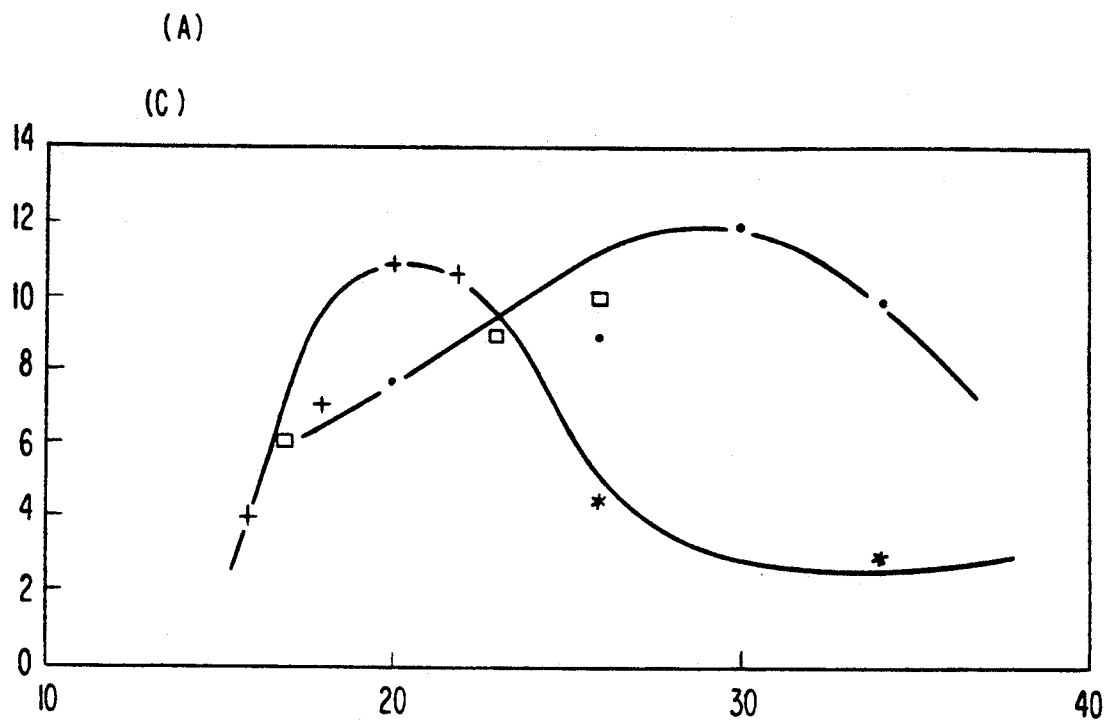
FIG. 1 is a plot of conversion (ICS/TOTAL C5) in an isomerization reaction of pentane to isopentane according to the invention vs. framework $SiO_2/AlO_2$ ratio.

The present invention refers to a process for the obtainment of a new light paraffin isomerization catalyst with an optimum Al (framework):extraframework Al ratio that has a high activity and selectivity of branched isomers.

The catalyst consists of 50 to 97% by weight of a modified mordenite with a $SiO_2/Al_2O_3$ framework ratio between 15 and 40, between 59 and 1% of a refractory metal oxide (preferably $Al_2O_3$) and a metal of group VIII and particularly platinum, palladium or Ni, in an amount of 0.1 to 0.5 by weight referred to the total of the catalyst. The preferred metal of group VIII is platinum.

The starting mordenite can be natural or synthetic and it will preferably be found in acid form. The methods to convert the sodium form into the acid form of mordenite are well known in the prior art. In this case exchange with an ammonium salt followed by calcination to remove the $NH_3$ and to elave the protonic form, or else direct treatment of the sodium mordenite with a mineral acid is preferred.

Acid mordenites obtained this way have a $SiO_2/Al_2O_3$ ratio between 13 and 18 and are treated with an acid solution preferably of strong mineral acids: HCl, $H_2SO_4$, $HNO_3$, $H_3PO_4$, etc.

Hydrochloric and sulfuric acids are the ones preferred in this invention.

The treatment temperature must be between 40° and 100° C., better between 60° and 90° C., and the contact time of the catalyst with the acid solution will be between 1 and 8 hours, preferably between 2 and 6 hours. The liquid/solid (volume: weight) ratio will be between 5 and 20, preferably between 8 and 15. The acid concentration must be between 1 and 6N and preferably between 2 and 5N. This acid treatment permits obtainment of mordenites with a $SiO_2/Al_2O_3$ ratio between 15 and 22 and with the minimum extraframework Al.

There is also the possibility of effecting initial acid treatment of the sodium mordenite and a subsequent exchange with $NH_4^+$ to obtain the protonic form, or to treat the sodium form of the two above cases a $SiO_2/Al_2O_3$ ratio similar to the one obtained in the acid treatment described in the first place can be attained.

The mordenite obtained in the previous treatment, either in the acid or ammonium form, is heated in the presence of a stream of gas that contains oxygen and steam, preferably air/steam. The percentage of steam in the stream of gas must be between 5 and 100%, preferably between 15 and 80, (by volume.) The treatment temperature will be between 300° and 600° C., preferably between 350° and 500° C. and the treatment time between 2 and 8 hours, preferably between 2 and 6 hours.

The zeolite obtained by this treatment has a $SiO_2/Al_2O_3$ ratio between 15 and 40, preferably between 22 and 35, and a framework Al/extraframework Al ratio between 1 and 10, preferably between 1 and 5, and it must be mixed with an inorganic refractory oxide, preferably alumina in a zeolite/oxide proportion between 1:1 and 99:1 or between 50% and 1% oxide in the zeolite/oxide mixture.

The metal that furnishes the hydrogenating function to the catalyst must be of group VIII, preferably Pt, and it must be found in m amount from 0.1 to 0.5% by weight, referred to the total of the catalyst. The metal can deposit on the mordenite, on the alumina or on a mixture of the two. In our case it is preferred to add platinum on the zeolite/alumina mixture.

The Pt deposition method can be by impregnation or by exchange with a competing ion or without one and with chloroplatinic acid or any amine Pt complex (for ex. Keller salt.)

In the present invention it is preferred to impregnate the mordenite with a solution of chloroplatinic acid/HCl where the concentration of HCl is between 0.05 and 1N, preferably between 0.1 and 0.5N. The liquid/solid (l/kg) ratio must be between 1 and 10, preferably between 2 and 5.

The dry product is normally calcined at temperatures between 300° and 600° C. in an air atmosphere to obtain the final catalyst.

Before it is used as an isomerization catalyst, the catalyst must be reduced in a stream of hydrogen at a temperature between 300° and 500° C.

The catalyst that the invention refers to is useful in catalytic isomerization of short chain ($C_5$ to $C_7$) light straight run and very especially in the refinery LSR stream.

The isomerization reaction can be carried out at a temperature range of 150° to 400° C. and space velocities of 0.5 to 4 h$^{-1}$ and under a total hydrogen pressure that will be between 10 and 50 bars. The molar hydrogen/hydrocarbon ratio must be between 0.5 and 4.

EXAMPLES

A series of non-restrictive examples in which the catalysts prepared by our method are compared with others prepared by different methods claimed up to now and covering a broad spectrum of $SiO_2/Al_2O_3$ framework ratios from 14 to 62 and framework Al/extraframework Al ratios from 0 to 10 are given in this part.

EXAMPLE 1

This example is carried out in accordance with the invention.

A Norton commercial acid mordenite with a $SiO_2/Al_2O_3$ ratio=14 was treated with 3N hydrochloric acid for 6 hours at 80° C. and with a liquid/solid (liters/-kilo) ratio of 10.

The mordenite obtained this way had a $SiO_2/Al_2O_3$ ratio of 22 and it was subsequently treated with air/-steam mixtures for 3.5 hours. The treatment temperature was 400° C. In the following tables one can see the treatment conditions with steam-air and the $SiO_2/Al_2O_3$ ratios attained for the catalysts given in this example.

| Catal. No | % in vol. of $H_2O$* | t (hr.) | Trat. t. °C. | ($SiO_2/Al_2O_3$) framework | Framework Al/ Extraframework Al |
|---|---|---|---|---|---|
| 1A | 100 | 3.5 | 400 | 20 | 9 |
| 1B | 3 | " | " | 26 | 5.25 |
| 1C | 20 | " | " | 30 | 2.97 |
| 1D | 84 | " | " | 34 | 1.84 |

*In the air/steam mixture

The zeolites treated this way were mixed with $\delta Al_2O_3$ in a ratio of 8:2 and they were impregnated with a solution of $H_2PtCl_4$ in 0.2N HCl such that the Pt content in the final catalysts was 0.35% by weight.

The catalysts were calcined at 300° C. for 3 hours and at 450° C. for 1 hour and were subjected to a reduction process at 300° C. with $H_2$ before evaluating their activity.

EXAMPLE 2

It has been carried out with a process different from the one claimed here and it is given for comparison purposes.

As of the same commercial acid mordenite of example 1 four catalysts were prepared by different acid treatments of the same. The reaction conditions as well as the $SiO_2/Al_2O_3$ framework ratios attained can be seen in the following table:

| Catal. No | (HCl) | T (°C.) | t (h) | Liq/Sol | $SiO_2/Al_2O_3$ (framework) |
|---|---|---|---|---|---|
| 2A | 3 | 80 | 6 | 10 | 20 |
| 2B | 3.5 | 90 | 6 | 10 | 22 |
| 2C | 3 | 80 | 3 | 4 | 18 |
| 2D | — | — | — | — | 16 |

The treated mordenites were mixed with $\delta Al_2O_3$, Pt was added and they were calcined, as in example 1.

EXAMPLE 3

It has been carried out with a process different from the one claimed here and it is given for comparison purposes.

As of the commercial acid mordenite of the previous examples. 3 catalysts were prepared by calcination treatments in 100% $H_2O$ atmosphere at different temperatures.

The treatment conditions and the $SiO_2/Al_2O_3$ ratios obtained can be seen in the following table:

| Catal. No | T (°C.) | t (h) | $SiO_2/Al_2O_3$ (framework) | Framework Al/extra framework Al |
|---|---|---|---|---|
| 3A | 450 | 3 | 26 | 1.16 |
| 3B | 500 | 3 | 34 | 0.7* |
| 3C | 600 | 3 | 64 | 0.34 |

The mordenites treated with steam were mixed with $Al_2O_3$ and Pt was added as in example 1.

EXAMPLE 4

It has been carried out with a process different from the one claimed here and it is given for comparison purposes.

From the commercial acid mordenite of the above examples several catalysts, 4A, 4B and 4C were prepared by treatments with moisture saturated air at room temperature for 3.5 hours. The treatment temperature was 400° C. and this was repeated twice for catalyst 4C. Treated mordenite 4B was subjected afterwards to an exchange process with $NH_4^+$ calcination twice. The exchange was done with 2.5N $NH_4Cl$ at a temperature of 80° C. for 1 hour with a liquid:solid (volume/weight) ratio of 10. The calcination was done at 350° C. for 2 hours and at 500° C. for 3 hours. The $SiO_2/Al_2O_3$ reached can be seen in the following table:

| Catal. No | $SiO_2/Al_2O_3$ (framework) | Al (framework)/Al (extraframework) |
|---|---|---|
| 4A | 17 | 4.67 |
| 4B | 23 | 1.55 |
| 4C | 26 | 1.16 |

The mordenites treated by this method were mixed with $\delta Al_2O_3$ and platinum was added thereto as in example 1.

EXAMPLE 5

The catalysts prepared with and without the process of the invention were tested by the isomerization reaction of $nC_5$ and $nC_6$ in a flux microreactor. The reaction conditions tested were the following:

| Feed: | 60% $nC_5$ and 40% $nC_6$ |
|---|---|
| Pressure: | 30 Atm. |
| Temperature: | 250° C. |
| LHSV: | 35 $h^{-1}$ |
| $H_2$/hydrocarbon: | 1 (molar) |

The results of conversion from pentane to isopentane as contrasted with the $SiO_2/Al_2O_3$ ratio are shown in Table 1 and in FIG. 1.

One can observe that with other methods of preparation of the catalysts which are not in accordance with the invention and as pointed out in the prior art, the maximum activity for isomerization is found at a $SiO_2/Al_2O_3$ ratio between 17 and 23. In the catalysts prepared by our process, the maximum activity reaches higher $SiO_2/Al_2O_3$ ratios by virtue of the synergic effect upon the acidity which the extraframework Al has. The activity for isomerization of the catalyst which has the maximum prepared by our method is even higher than the maximum of the catalysts prepared by other methods. Besides, since the catalysts prepared by our method have a higher $SiO_2/Al_2O_3$ framework ratio, a greater coking resistance is to be expected.

Figure 2:
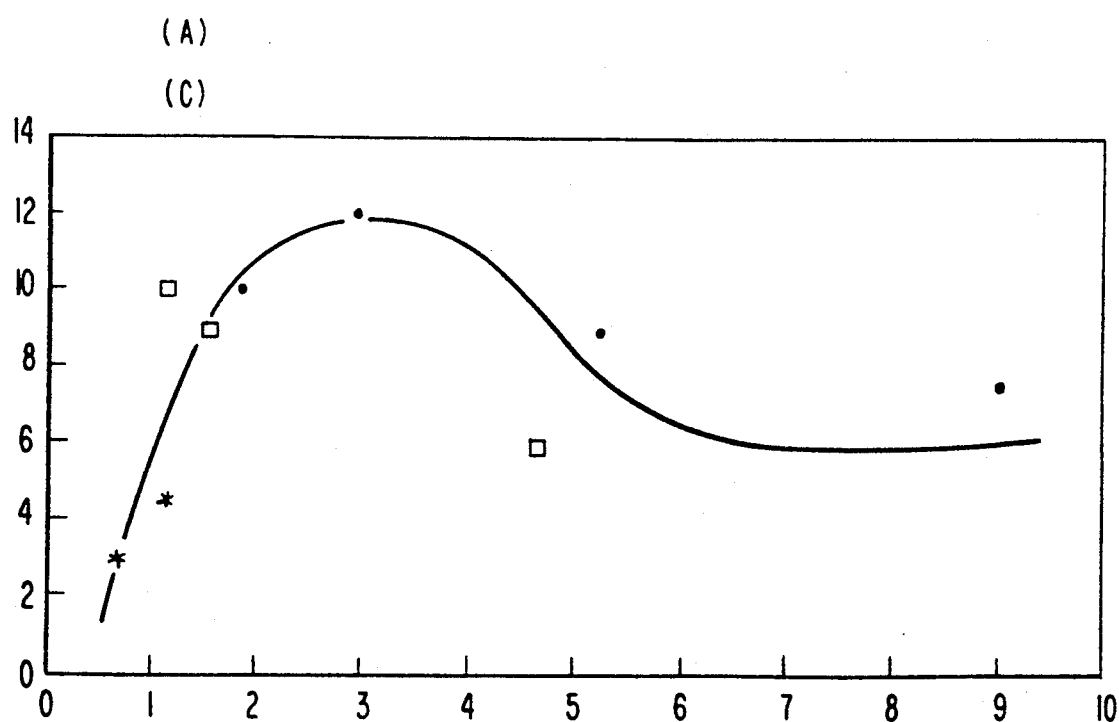
FIG. 2 is a plot of conversion (as per FIG. 1) v. (framework aluminum)/(extra framework aluminum).

The framework Al/extraframework Al ratio in contrast with the activity for isomerization of the catalysts presented in the figures is represented in FIG. 2. One can see how a maximum activity at certain framework Al/extraframework Al ratios which illustrates the above mentioned fact, the increase of the Bronsted acidity by the extraframework species produced upon preparing the catalyst by our process, is produced.

EXAMPLE 6

In this example the results obtained in a pilot plant with actual feed (refinery LSR stream) for the catalysts that have activity maximum in accordance with example 5 are shown.

The experiments were carried out at a pressure of 30 atm., a temperature of 250° C., a LSHV of 1 h$^{-1}$ and a H$_2$/hydrocarbon ratio of 1 molar. The composition of the added material and the results are shown hereinafter:

| Composition | % weight |
|---|---|
| C$_1$-C$_4$ | 0.05 |
| iC$_5$ | 42 |
| nC$_5$ | 51.7 |
| 2.2 MDI C$_4$ | 0.4 |
| 2 Me C$_5$ | 3.9 |
| 3 Me C$_5$ | 0.14 |
| nC$_6$ | 0.03 |
| Benzene | — |
| Sulfur (ppm) | 10 |
| Water (ppm) | — |

| Catalyst | iC$_5$/Total C$_5$ | Total gases/hydrocarbons* | RON (calculated) |
|---|---|---|---|
| 1-C | 68.2 | 2.0 | 82.0 |
| 2-A | 67.5 | 1.89 | 80.5 |

*(% weight)

It can be seen in the above table how isoparaffin/paraffin ratios close to balance with high octane numbers and low productivity of gases were attained for the catalyst prepared by our process.

TABLE 1

| Catalyst | SiO$_2$/Al$_2$O$_3$ (framework) | (Framework) Al/(extraframework) Al | iC$_5$/C$_5$ total (%) |
|---|---|---|---|
| 1A | 20 | 9 | 7.7 |
| 1B | 26 | 5.25 | 9 |
| 1C | 30 | 2.97 | 12 |
| 1D | 34 | 1.84 | 10 |
| 2A | 20 | — | 11 |
| 2B | 22 | — | 10.7 |
| 2C | 18 | — | 7 |
| 2D | 16 | — | 4 |
| 3A | 26 | 1.16 | 4.5 |
| 3B | 34 | 0.7 | 3 |
| 3C | 64 | 0.34 | 1 |
| 4A | 17 | 4.67 | 6 |
| 4B | 23 | 1.55 | 9 |

TABLE 1-continued

| Catalyst | SiO$_2$/Al$_2$O$_3$ (framework) | (Framework) Al/(extraframework) Al | iC$_5$/C$_5$ total (%) |
|---|---|---|---|
| 4C | 26 | 1.16 | 10 |

LEGENDS FOR THE FIGURES

FIG. 1:
(A) Isomerization of light paraffins. Conversion vs. SiO$_2$/Al$_2$O$_3$ ratio
(B) Silica(alumina (framework)
(C) IC$_5$/Total C$_5$
• Example 1
+ Example 2
☐ Example 3
☐ Example 4

FIG. 2:
(A) Isomerization of light paraffins. Conversion vs. framework Al/extraframework Al
(B) Framework Al/extraframework Al
(C) IC$_5$/Total C$_5$
Example 1
Example 3
Example 4

We claim:

1. A method for effecting light-paraffin isomerization of hydrocarbons which comprises the steps of: subjecting hydrocarbons to a temperature between about 150° and about 400° C. in the presence of hydrogen at a total hydrogen pressure of about 10 and about 50 bars at a space velocity LHSV between about 0.5 and about 4 hr$^{-1}$ and at a hydrogen to hydrocarbon ratio between 0.5 and about 4 in the presence of an isomerization catalyst which has been made by a process comprising the steps of:

(a) treating a mordenite with an acid solution at a temperature of between 40° to 100° C. to increase the framework SiO$_2$/Al$_2$O$_3$ ratio to between 15 and 22;

(b) contacting said mordenite with a gas stream comprising oxygen and steam at a temperature of between 300° and 600° C. to generate sufficient extra framework aluminum to bring the framework/extra framework aluminum ratio to between 1 and 10;

(c) mixing said mordenite with inorganic refractory oxide at a mordenite/inorganic refractory oxide ratio between about 1:1 to 99:1 to form a mixture;

(d) depositing a group VIII metal onto the said mordenite, said oxide or said mixture to form a catalyst;

(e) calcining said catalyst at a temperature of between 300° and 600° C.; and (f) reducing said catalyst in the presence of hydrogen gas at a temperature between 300° and 500° C. to form said isomerization catalyst.

2. The method according to claim 1 wherein said hydrocarbons comprise mixtures of hydrocarbons.

3. The method according to claim 2, wherein said hydrocarbons contain 4 to 7 carbon atoms.

* * * * *

UNITED STATES PATENT AND TRADEMARK OFFICE
CERTIFICATE OF CORRECTION

PATENT NO. : 5,264,648
DATED : November 23, 1993
INVENTOR(S) : Lazaro Munoz et al.

It is certified that error appears in the above-identified patent and that said Letters Patent is hereby corrected as shown below:

On the title page:

Item [30] Foreign Application Priority Data, the priority application number is incorrectly listed as "89025553" and should read "8902553". The priority application number was correctly listed in the Declaration.

Signed and Sealed this

Twenty-fourth Day of May, 1994

Attest:

BRUCE LEHMAN

Attesting Officer

Commissioner of Patents and Trademarks